United States Patent [19]

Nishii et al.

[11] Patent Number: 5,463,103
[45] Date of Patent: Oct. 31, 1995

[54] PROCESS FOR PRODUCING 1,4-DICYANO-2-BUTENE

[75] Inventors: Shinji Nishii, Niihama; Shigeo Wake, Saijo; Takeshi Ogawa, Niihama, all of Japan

[73] Assignee: Sumitomo Chemical Company, Limited, Osaka, Japan

[21] Appl. No.: 210,412

[22] Filed: Feb. 24, 1994

[30] Foreign Application Priority Data

Feb. 26, 1993 [JP] Japan .................................. 5-038313
Nov. 24, 1993 [JP] Japan .................................. 5-293055

[51] Int. Cl.$^6$ ...................... C07C 253/10; C07C 253/16
[52] U.S. Cl. ........................ 558/341; 558/335; 558/350
[58] Field of Search ................................... 558/335, 341, 558/350

[56] References Cited

U.S. PATENT DOCUMENTS 3,711,527  1/1973  Kurtz .................................. 260/465.8

FOREIGN PATENT DOCUMENTS 0563859  10/1993  European Pat. Off. .
857374   10/1952  Germany .
2102263  8/1972   Germany .
2144390  3/1973   Germany .
2723778  4/1979   Germany .
2714799  10/1979  Germany .
1384796  2/1975   United Kingdom .

Primary Examiner—Joseph Paul Brust
Attorney, Agent, or Firm—Birch, Stewart, Kolasch & Birch

[57] ABSTRACT

The object of the present invention is to provide a process for producing 1,4-dicyano-2-butene in a high yield and in an industrially advantageous way.

The present invention relates to a process for producing 1,4-dicyano-2-butene which comprises reacting a butene derivative represented by the formula [1]

$$R_1-CH_2-CH=CH-CH_2-R_2 \quad [1]$$

or the formula [2]

$$R_3-CH_2-CHR_4-CH=CH_2 \quad [2]$$

wherein each of $R_1$ and $R_3$ represents a hydroxy group, lower acyloxy group, lower alkoxy group or cyano group; and each of $R_2$ and $R_4$ represents a hydroxy group, lower acyloxy group or lower alkoxy group, with hydrogen cyanide in the presence of a catalyst comprising a product prepared from a cuprous halide, a non-aromatic amine hydrohalide and at least one member selected from the group consisting of Lewis acids and basic compounds.

9 Claims, No Drawings

PROCESS FOR PRODUCING 1,4-DICYANO-2-BUTENE

FIELD OF THE INVENTION

The present invention relates to a process for producing 1,4-dicyano-2-butene. 1,4-Dicyano-2-butene is useful as a material for synthesizing hexamethylenediamine, which is a material for 6,6-nylon and other products.

BACKGROUND OF THE INVENTION

Several processes are known which may be used for producing 1,4-dicyano-2-butene from butene derivatives and hydrogen cyanide. (1) GB No. 1,384,796 discloses a process for producing 1,4-dicyano-2-butene which comprises reacting 2-butene-1,4-diol with hydrogen cyanide in a gas phase by using a catalyst comprising a cuprous halide supported on silica gel or the like. (2) German Patent No. 2,144,390 discloses a process for producing 1,4-dicyano-2-butene by reacting 2-butene-1,4-diol with hydrogen cyanide in an aqueous phase in the presence of a catalyst comprising cuprous bromide and an alkali metal bromide. (3) U.S. Pat. No. 3,711,527 discloses a process for producing 1,4-dicyano-2-butene by reacting 1,4-diacetoxy-2-butene with hydrogen cyanide in a liquid in the presence of a catalyst comprising a cuprous halide and a non-aromatic amine hydrohalide.

However, the aforesaid processes are all not fully satisfactory from the industrial viewpoint. The process (1) forms a large amount of impurities and gives a low yield. The process (2) shows a poor volume efficiency (that is, the ratio of the amount of the product formed to the total volume of the reaction system). The process (3) shows a low selectivity to the intended product.

SUMMARY OF THE INVENTION

An object of the present invention is to provide a process for producing 1,4-dicyano-2-butene in a high yield and in an industrially advantageous way.

Other objects and advantages of the present invention will become apparent from the description that follows.

The present inventors have made extensive study on the process for producing 1,4-dicyano-2-butene by the reaction of butene derivatives with hydrogen cyanide and resultantly found that a process which uses a catalyst comprising a product prepared from a cuprous halide, a non-aromatic amine hydrohalide and at least one member selected from the group consisting of Lewis acids and basic compounds can achieve the above-mentioned objects. The present invention has been attained on the basis of above finding.

Thus, according to the present invention, there is provided a process for producing 1,4-dicyano-2-butene which comprises reacting a butene derivative represented by the formula [1]

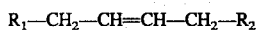   [1]

or the formula [2]

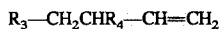   [2]

wherein $R_1$ and $R_3$ are the same or different and each represents a hydroxy group, a lower acyloxy group, a lower alkoxy group or a cyano group; and $R_2$ and $R_4$ are the same or different and each represents a hydroxy group, a lower acyloxy group or a lower alkoxy group, with hydrogen cyanide in the presence of a catalyst comprising a product prepared from a cuprous halide, a non-aromatic amine hydrohalide and at least one member selected from the group consisting of Lewis acids and basic compounds.

DETAILED DESCRIPTION

The present invention is described in detail below.

The butene derivatives [1] or [2] to be used in the present invention may be, for example, butenediols such as 2-butene-1,4-diol and 3-butene-1,2-diol; 1,4- or 1,2-dilower acyloxy-2 or 3-butenes such as 1,4-diacetoxy-2-butene, 1,2-diacetoxy-3-butene, 1,4-dipropionyloxy-2-butene, 1,2-dipropionyloxy-3-butene, 1,4-dibutyryloxy-2-butene, 1,2-dibutyryloxy-3-butene, 1,4-divaleryloxy-2-butene and 1,2-divaleryloxy-3-butene; 1,4- or 1,2-dilower alkoxy-2 or 3-butenes such as 1,4-dimethoxy-2-butene, 1,2-dimethoxy-3-butene, 1,4-dipropoxy-2-butene, 1,2-diethoxy-3-butene, 1,4-dipropoxy-2-butene, 1,2-dipropoxy-3-butene, 1,4-dibutoxy-2-butene, 1,2-dibutoxy-3-butene, 1,4-dipentoxy-2-butene and 1,2-dipentoxy-3-butene; 5- or 3-hydroxy-3 or 4-pentenenitriles such as 5-hydroxy-3-pentenenitrile and 3-hydroxy-4-pentenenitrile; 5- or 3-lower acyloxy-3 or 4-pentenenitriles such as 5-acetoxy-3-pentenenitrile, 3-acetoxy-4-pentenenitrile, 5-propionyloxy-3-pentenenitrile, 3-propionyloxy-4-pentenenitrile, 5-butyryloxy-3-pentenenitrile, 3-butyryloxy-4-pentenenitrile, 5-valeryloxy-3-pentenenitrile and 3-valeryloxy-4-pentenenitrile; and 5- or 3-lower alkoxy-3 or 4-pentenenitriles such as 5-methoxy-3-pentenenitrile, 3-methoxy-4-pentenenitrile, 5-ethoxy-3-pentenenitrile, 3-ethoxy-4-pentenenitrile, 5-propoxy-3-pentenenitrile and 3-propoxy-4-pentenenitrile, 5-butoxy-3-pentenenitrile, 3-butoxy-4-pentenenitrile, 5-pentoxy-3-pentenenitrile and 3-pentoxy-4-pentenenitrile. These butene derivatives [1] or [2] may be used each alone or as a mixture thereof. Preferred among them are 1,4- or 1,2-dilower acyloxy-2 or 3-butenes; more preferred is 1,4-diacetoxy-2-butene.

The butene derivatives [1] or [2] may be prepared by known methods. For example, 1,4- or 1,2-dilower acyloxy-2- or 3-butenes may be prepared from butadiene and a lower carboxylic acid. Butenediols may be easily obtained by the hydrolysis of 1,4- or 1,2-dilower acyloxy-2 or 3-butenes. 1,4- or 1,2-Dilower alkoxy-2 or 3-butenes may be prepared from butadiene and a lower alcohol. Further, 5- or 3-hydroxy-3 or 4-pentenenitriles, 5- or 3-lower acyloxy-3 or 4-pentenenitriles, and 5- or 3-lower alkoxy-3 or 4-pentenenitriles may be prepared by reacting, respectively, butenediols, 1,4- or 1,2-dilower acyloxy-2- or 3-butenes and 1,4- or 1,2-dilower alkoxy-2 or 3-butenes with hydrogen cyanide. When 1,4- or 1,2-dilower acyloxy-2 or 3-butenes, or 1,4- or 1,2-dilower alkoxy-2 or 3-butenes are used in the process of the present invention, 5- or 3-hydroxy-3 or 4-pentenenitriles, 5- or 3-lower acyloxy-3 or 4-pentenenitriles, or 5- or 3-lower alkoxy-3 or 4-pentenenitriles may be partly formed. These products can be reused as the starting material. The butene derivatives [1] or [2] may be provided to the reaction system either continuously or intermittently.

The hydrogen cyanide used in the present invention is preferably anhydrous hydrogen cyanide or a hydrocyanic acid of high concentration (usually having a water content of 10% by weight or less). The amount thereof to be used is generally about 100–300% by mole to the butene derivatives [1] or [2]. The hydrogen cyanide may be provided to the reaction system either continuously or intermittently.

The cuprous halide to be used in the catalyst comprising a product prepared from a cuprous halide, a non-aromatic amine hydrohalide and at least one member selected from the group consisting of Lewis acids and basic compounds is preferably cuprous chloride or cuprous bromide.

The non-aromatic amine hydrohalides to be used are preferably those which can form a molten mixture with a cuprous halide. Examples thereof include the hydrohalides of lower alkylamines such as methylamine, dimethylamine, trimethylamine, ethylamine, diethylamine, triethylamine, tripropylamine and tributylamine; the hydrohalides of amines having a functional group inert to the reaction, e.g., hydroxyalkylamines such as N,N-dimethylethanolamine and N-methyldiethanolamine and diamines such as N,N,N',N'-tetramethylethylenediamine. The hydrohalides include hydrochlorides, hydrobromides, and the like.

Specific examples of the Lewis acid include zinc chloride, zinc bromide, zinc iodide, nickel chloride, nickel bromide, magnesium chloride, magnesium bromide, magnesium iodide, lithium chloride, lithium bromide, lithium iodide, ferrous chloride, ferric chloride, ferrous bromide, ferric bromide, aluminum chloride, aluminum bromide, and the like.

The basic compound may be, for example, acetates, such as sodium acetate, potassium acetate, lithium acetate and ammonium acetate; carbonates, such as sodium carbonate and potassium carbonate and bicarbonates, such as sodium bicarbonate and potassium bicarbonate.

The molar ratio of the non-aromatic amine hydrohalide to the cuprous halide in the catalyst is usually 1/3 to 3, preferably about 2/3 to 1.5, more preferably about 1. The ratio of the Lewis acid to the cuprous halide is usually about 10–100% by mole. The ratio of the basic compound to the cuprous halide is usually about 10–50% by mole.

The amount of the catalyst to be used is about 10–200% by mole, preferably 50–100% by mole to the butene derivative [1] or [2], in terms of cuprous halide.

The catalyst is prepared usually by heating and melting a cuprous halide, a non-aromatic amine hydrohalide and at least one member selected from the group consisting of Lewis acids and basic compounds. The heating temperature is not critical so long as it ensures the melting of the catalyst. It is usually about 60°–200° C., preferably 80°–120° C.

The reaction of the butene derivative [1] or [2] with hydrogen cyanide is generally conducted in a liquid phase by preparing the catalyst by heating and then providing the butene derivative [1] or [2] and hydrogen cyanide to the catalyst. If necessary, aging can be conducted after providing the butene derivative [1] or [2] and hydrogen cyanide. The butene derivative [1] or [2] and hydrogen cyanide may be provided either each individually or after the two reactants have been mixed in advance.

The present reaction is conducted usually at a atmospheric pressure, optionally under applied pressure. The reaction is preferably conducted in an atmosphere of inert gas, such as nitrogen. The reaction temperature is usually in the range of about 20°–200° C., preferably about 60°–140° C. The reaction time may be suitably determined by tracing the change in the amount of the starting material and the product through, for example, chromatography. When the time of completion of the reaction can be preestimated, alternatively, the reaction may be stopped after the lapse of a predetermined time.

After the reaction, the reaction mixture is subjected to aftertreatments in a conventional manner. For example, the intended product is extracted with a solvent, such as ethyl acetate and toluene, to separate the catalyst and then the solvent is distilled off from the extract to obtain 1,4-dicyano-2-butene. If necessary, the 1,4-dicyano-2-butene may be subjected to further purification treatments, such as distillation or recrystallization. The resulting product is used, for example, as the material for synthesizing hexamethylenediamine or the like.

The recovered catalyst separated from the intended product can be reused as the catalyst without any treatment or after removing the water, alcohols or organic acids which are formed in the reaction or after-treatment and contained in the recovered catalyst by such means as vacuum distillation. The recovered catalyst tends to solidify when allowed to stand at room temperature for a long time, so the recovered catalyst is usually treated and stored at a temperature higher than room temperature. The reuse of the recovered catalyst can be conducted repeatedly.

In reusing the recovered catalyst, a hydrogen halide is favorably added to the catalyst because the deterioration of the catalyst can be effectively prevented thereby, to enable repeated reusing of the catalyst over a longer period. The hydrogen halide may be, for example, hydrogen chloride, hydrogen bromide, and the like. The hydrogen halides may be used in any of the forms of aqueous solution, gas, and solution in an organic solvent. The amount of the hydrogen halide used is usually about 0.01–0.1 mole per 1 mole of the cuprous halide used in the catalyst.

The hydrogen halide may be added either to the reaction mixture after the reaction or to the recovered catalyst separated from the intended product. In the case where the hydrogen halide is added to the recovered catalyst separated from the intended product and when the recovered catalyst is reused after removal of water, alcohols and organic acids contained therein, the hydrogen halide may be added either before or after the removal. Further, when an insoluble substance is formed owing to deterioration of the catalyst in the course of separation and recovery of the catalyst, the hydrogen halide may also be added to the mixture of the catalyst and the insoluble substance or to the insoluble substance after separation.

According to the present invention, 1,4-dicyano- 2-butene can be obtained in a good yield, high selectivity and good volume efficiency. Further, the aftertreatments of the reaction can be conducted easily and the production facilities can be simplified. Moreover, the catalyst can be recycled and reused, so that the consumption of the catalyst can be reduced. Thus, the present process is of great industrial advantage.

The present invention will be described in more detail below with reference to Examples. However, the invention is not limited to such Examples. In the Examples, the "conversion" refers to the conversion of butene derivative [1] or [2] and the "yield" to the value calculated in terms of pure 1,4-dicyano-2-butene.

EXAMPLE 1

Cuprous chloride (9.9 g, 0.1 mole), trimethylamine hydrochloride (9.6 g, 0.1 mole) and zinc chloride (8.18 g, 0.06 mole) were heated at 100° C. with stirring to prepare a molten catalyst liquid. Then a mixture of 1,4-diacetoxy-2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 0.5 hour and then extracted 4 times with 15 ml of ethyl acetate. Then the solvent was evaporated off under reduced pressure to obtain a crude 1,4-dicyano-2-butene (conversion: 99%, yield: 63%).

EXAMPLE 2

Cuprous chloride (9.9 g, 0.1 mole), trimethylamine hydrochloride (9.6 g, 0.1 mole) and nickel chloride (3.89 g, 0.03 mole) were heated at 120° C. with stirring to prepare a molten catalyst liquid. Then a mixture of 1,4-diacetoxy-2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 0.5 hour and then extracted 4 times with 15 ml of ethyl acetate. Then the solvent was evaporated off under reduced pressure to obtain a crude 1,4-dicyano- 2-butene (conversion: 95%, yield: 61%).

EXAMPLE 3

Cuprous chloride (9.9 g, 0.1 mole), trimethylamine hydrochloride (9.6 g, 0.1 mole), zinc chloride (8.18 g, 0.06 mole) and sodium acetate (1.64 g, 0.02 mole) were heated at 100° C. with stirring to prepare a molten catalyst liquid. Then a mixture of 1,4-diacetoxy- 2-butene (17.2 g, 0.1 mole) and hydrogen cyanide (7.6 ml, 0.2 mole) was added dropwise into the molten catalyst liquid at 100° C. over a period of 2.5 hours. The resulting reaction mixture was kept at 100° C. for further 1 hour and then extracted 4 times with 15 ml of ethyl acetate. Then the solvent was evaporated off under reduced pressure to obtain a crude 1,4-dicyano-2-butene (conversion: 97%, yield: 88%).

EXAMPLE 4

Cuprous chloride (4.95 g, 0.05 mole), trimethylamine hydrochloride (4.78 g, 0.05 mole), zinc chloride (6.81 g, 0.05 mole) and sodium acetate (0.82 g, 0.01 mole) were heated at 100° C. with stirring to prepare a molten catalyst liquid. Then a mixture of 1,4-diacetoxy- 2-butene (17.2 g, 0.1 mole) and hydrogen cyanide (7.6 ml, 0.2 mole) was added dropwise into the catalyst liquid at 100° C. over a period of 3.5 hours. The resulting reaction mixture was kept at 100° C. for further 1 hour and then extracted 4 times with 15 ml of ethyl acetate. Then the solvent was evaporated off under reduced pressure to obtain a crude 1,4-dicyano-2-butene (conversion: 91%, yield: 73%).

EXAMPLE 5

Cuprous chloride (9.9 g, 0.10 mole), dimethylamine hydrochloride (8.16 g, 0.1 mole), zinc chloride (5.45 g, 0.04 mole) and sodium acetate (1.64 g, 0.02 mole) were heated at 120° C. with stirring to prepare a molten catalyst liquid. Then a mixture of 1,4-diacetoxy-2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 1 hour and then extracted 4 times with 15 ml of ethyl acetate. Then the solvent was evaporated off under reduced pressure to obtain a crude 1,4-dicyano-2-butene (conversion: 96%, yield: 90%).

EXAMPLE 6

Cuprous chloride (9.9 g, 0.1 mole), trimethylamine hydrochloride (9.6 g, 0.1 mole), zinc chloride (5.45 g, 0.04 mole) and sodium bicarbonate (1.68 g, 0.02 mole) were heated at 100° C. with stirring to prepare a molten catalyst liquid. Then a mixture of 1,4-diacetoxy- 2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 1 hour and then extracted 4 times with 15 ml of ethyl acetate. Then the solvent was evaporated off under reduced pressure to obtain a crude 1,4-dicyano-2-butene (conversion: 96%, yield: 85%).

EXAMPLE 7

Cuprous chloride (9.9 g, 0.1 mole), trimethylamine hydrochloride (9.6 g, 0.1 mole) and sodium acetate (1.64 g, 0.02 mole) were heated at 100° C. with stirring to prepare a molten catalyst liquid. Then a mixture of 1,4-diacetoxy-2-butene (17.2 g, 0.1 mole) and hydrogen cyanide (7.6 ml, 0.2 mole) was added dropwise into the catalyst liquid at 100° C. over a period of 3 hours. The resulting reaction mixture was kept at 100° C. for further 2 hours and then extracted 4 times with 30 ml of toluene. Then the solvent was evaporated off under reduced pressure to obtain a crude 1,4-dicyano-2-butene (conversion: 96%, yield: 60%).

EXAMPLE 8

Cuprous chloride (4.95 g, 0.05 mole), trimethylamine hydrochloride (4.78 g, 0.05 mole), zinc chloride (2.72 g, 0.02 mole) and sodium acetate (0.82 g, 0.01 mole) were heated at 100° C. with stirring to prepare a molten catalyst liquid. Then a mixture of 1,4-dimethoxy- 2-butene (5.8 g, 0.05 mole) and hydrogen cyanide (3.8 ml, 0.1 mole) was added dropwise into the catalyst liquid at 100° C. over a period of 3 hours. The resulting reaction mixture was kept at 100° C. for further 2 hours and then extracted 4 times with 30 ml of toluene. Then the solvent was evaporated off under reduced pressure to obtain a crude 1,4-dicyano-2-butene (conversion: 99%, yield: 33%).

EXAMPLE 9

Cuprous chloride (4.95 g, 0.05 mole), trimethylamine hydrochloride (4.78 g, 0.05 mole), magnesium chloride (1.9 g, 0.02 mole) and sodium acetate (1.64 g, 0.02 mole) were heated at 100° C. with stirring to prepare a molten catalyst liquid. Then a mixture of 1,4-dimethoxy-2-butene (5.8 g, 0.05 mole) and hydrogen cyanide (3.8 ml, 0.1 mole) was added dropwise into the catalyst liquid at 100° C. over a period of 3 hours. The resulting reaction mixture was kept at 100° C. for further 2 hours and then extracted 4 times with 30 ml of toluene. Then the solvent was evaporated off under reduced pressure to obtain a crude 1,4-dicyano-2-butene (conversion: 99%, yield: 45%).

EXAMPLE 10

Cuprous chloride (4.95 g, 0.05 mole), trimethylamine hydrochloride (4.78 g, 0.05 mole) and lithium chloride (0.85 g, 0.02 mole) were heated at 100° C. with stirring to prepare a molten catalyst liquid. Then a mixture of 1,4-dimethoxy-2-butene (5.8 g, 0.05 mole) and hydrogen cyanide (3.8 ml, 0.1 mole) was added dropwise into the catalyst liquid at 100° C. over a period of 3 hours. The resulting reaction mixture was kept at 100° C. for further 2 hours and then extracted 4 times with 30 ml of toluene. Then the solvent was evaporated off under reduced pressure to obtain a crude 1,4-dicyano- 2-butene (conversion: 99%, yield: 37%).

EXAMPLE 11

Cuprous chloride (9.9 g, 0.1 mole), dimethylamine hydrochloride (8.16 g, 0.1 mole), zinc chloride (5.45 g, 0.04 mole) and sodium acetate (1.64 g, 0.02 mole) were heated at 120° C. with stirring to prepare a molten catalyst liquid. Then a mixture of 1,4-diacetoxy- 2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 2 hours and then extracted 4 times with 15 ml of toluene. Then the solvent was evaporated off under reduced pressure to obtain a crude 1,4-dicyano-2-butene. After the extraction, the catalyst liquid was recovered, concentrated hydrochloric acid (0.2 g, 0.002 mole) was added thereto at 70°–80° C., the resulting mixture was kept at the temperature for 30 min. and water was removed therefrom under reduced pressure. The catalyst liquid thus treated was recycled for use in the next reaction. The results of the reactions are shown in Table 1.

TABLE 1

| Number of times of recycle | Conversion (%) | Yield (%) |
|---|---|---|
| 1 | 93 | 53 |
| 2 | 97 | 67 |
| 3 | 97 | 67 |
| 4 | 98 | 68 |
| 5 | 97 | 68 |
| 6 | 97 | 67 |
| 7 | 98 | 70 |
| 8 | 97 | 67 |
| 9 | 98 | 69 |
| 10 | 98 | 71 |
| 11 | 96 | 64 |
| 12 | 95 | 57 |
| 13 | 96 | 65 |
| 14 | 96 | 67 |

Comparative Example 1

Cuprous chloride (9.9 g, 0.1 mole) and trimethylamine hydrochloride (9.6 g, 0.1 mole) were heated at 100° C. with stirring to prepare a molten catalyst liquid. Then a mixture of 1,4-diacetoxy-2-butene (17.2 g, 0.1 mole) and hydrogen cyanide (7.6 ml, 0.2 mole) was added dropwise into the catalyst liquid at 100° C. over a period of 2.5 hours. The resulting reaction mixture was kept at 100° C. for further 1 hour and then extracted 4 times with 15 ml of ethyl acetate. Then the solvent was evaporated off under reduced pressure to obtain a crude 1,4-dicyano-2-butene (conversion: 91%, yield: 46%).

Comparative Example 2

Cuprous chloride (4.95 g, 0.05 mole) and trimethylamine hydrochloride (4.78 g, 0.05 mole) were heated at 100° C. with stirring to prepare a molten catalyst liquid. Then a mixture of 1,4-dimethoxy-2-butene (5.8 g, 0.05 mole) and hydrogen cyanide (3.8 ml, 0.1 mole) was added dropwise into the catalyst liquid at 100° C. over a period of 3 hours. The resulting reaction mixture was kept at 100° C. for further 2 hours and then extracted 4 times with 30 ml of toluene. Then the solvent was evaporated off under reduced pressure to obtain a crude 1,4-dicyano-2-butene (conversion: 97%, yield 26%).

What is claimed is:

1. A process for producing 1,4-dicyano-2-butene which comprises reacting a butene derivative represented by the formula [1]

$$R_1-CH_2-CH=CH-CH_2-R_2 \quad [1]$$

or the formula [2]

$$R_3-CH_2-CHR_4-CH=CH_2 \quad [2]$$

wherein $R_1$ and $R_3$ are the same or different and each represents a hydroxy group, a lower alkylcarbonyloxy group, a lower alkoxy group or a cyano group; and $R_2$ and $R_4$ are the same or different and each represents a hydroxy group, a lower alkylcarbonyloxy group or a lower alkoxy group, with hydrogen cyanide in the presence of a catalyst comprising a product prepared from a cuprous halide, a lower alkylamine, hydroxyalkylamine or alkylenediamine hydrohalide and at least one member selected from the group consisting of Lewis acids and basic acetates, carbonates or bicarbonates.

2. The process according to claim 1 wherein the cuprous halide is cuprous chloride or cuprous bromide.

3. The process according to claim 1 wherein the hydrohalide is the hydrochloride or the hydrobromide of a lower alkylamine.

4. The process according to claim 3 wherein the hydrochloride or the hydrobromide of a lower alkylamine is the hydrochloride or the hydrobromide of methylamine, dimethylamine, trimethylamine, ethylamine, diethylamine or triethylamine.

5. The process according to claim 1 wherein said at least one member is zinc chloride, zinc bromide, zinc iodide, nickel chloride, nickel bromide, magnesium chloride, magnesium bromide, magnesium iodide, lithium chloride, lithium bromide, lithium iodide, ferrous chloride, ferric chloride, ferrous bromide or ferric bromide.

6. The process according to claim 1 wherein said at least one member is sodium acetate, potassium acetate, lithium acetate, ammonium acetate, sodium carbonate, potassium carbonate, sodium bicarbonate or potassium bicarbonate.

7. The process according to claim 1 wherein the butene derivative is 1,4-diacetoxy-2-butene.

8. The process according to any one of claims 1 to 7 which further comprises separating the used catalyst and reusing the separated used catalyst without any treatment or after removing from the catalyst the water, alcohols or organic acids contained therein.

9. The process according to any one of claims 1 to 7 which further comprises (1) separating the used catalyst,
(2)
  1) adding a hydrogen halide to the separated used catalyst and then removing from the catalyst the water, alcohols or organic acids contained therein, or
  2) removing from the separated used catalyst the water, alcohols or organic acids contained therein and then adding a hydrogen halide to the catalyst, and
(3) reusing the used catalyst thus treated.

* * * * *

UNITED STATES PATENT AND TRADEMARK OFFICE
CERTIFICATE OF CORRECTION

PATENT NO. : 5,463,103
DATED : October 31, 1995
INVENTOR(S) : Shinji Nishii et al.

It is certified that error appears in the above-indentified patent and that said Letters Patent is hereby corrected as shown below:

TITLE PAGE:
Please correct the application serial number shown in section [21] from "210,412" to read -- 201,412 --.

Signed and Sealed this

Twentieth Day of February, 1996

Attest:

BRUCE LEHMAN

Attesting Officer     Commissioner of Patents and Trademarks